(12) United States Patent
Wismer et al.

(10) Patent No.: US 9,061,958 B2
(45) Date of Patent: *Jun. 23, 2015

(54) SEPARATION OF R-1233 FROM HYDROGEN FLUORIDE

(71) Applicant: Arkema Inc., King of Prussia, PA (US)

(72) Inventors: John A. Wismer, Washington Crossing, PA (US); Benjamin Bin Chen, Wayne, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/264,374

(22) Filed: Apr. 29, 2014

(65) Prior Publication Data

US 2014/0231240 A1 Aug. 21, 2014

Related U.S. Application Data

(63) Continuation-in-part of application No. 13/257,740, filed as application No. PCT/US2010/027409 on Mar. 16, 2010, now Pat. No. 8,735,636.

(60) Provisional application No. 61/162,789, filed on Mar. 24, 2009.

(51) Int. Cl.
- C07C 17/38 (2006.01)
- C07C 17/383 (2006.01)
- B01D 3/36 (2006.01)

(52) U.S. Cl.
CPC ............ C07C 17/383 (2013.01); B01D 3/36 (2013.01)

(58) Field of Classification Search
None
See application file for complete search history.

(56) References Cited

U.S. PATENT DOCUMENTS

| | | | |
|---|---|---|---|
| 5,710,352 A | 1/1998 | Tung | |
| 5,877,359 A | 3/1999 | Elsheikh et al. | |
| 6,013,846 A | 1/2000 | Wismer et al. | |
| 6,844,475 B1 | 1/2005 | Tung et al. | |
| 7,183,448 B2 | 2/2007 | Nakada et al. | |
| 8,168,837 B2 | 5/2012 | Merkel et al. | |
| 8,519,201 B2 | 8/2013 | Merkel et al. | |
| 8,716,538 B2 | 5/2014 | Merkel et al. | |
| 8,735,636 B2 * | 5/2014 | Wismer et al. | 570/178 |
| 2008/0051612 A1 | 2/2008 | Knapp et al. | |

FOREIGN PATENT DOCUMENTS

JP 2006-124282 A 5/2006

* cited by examiner

Primary Examiner — Sudhakar Katakam
(74) Attorney, Agent, or Firm — Steven D. Boyd

(57) ABSTRACT

The invention relates to a process for separating monochlorotrifluoropropenes such as HCFC-1233 from azeotrope or azeotrope like combinations with HF. The process employs a cold, liquid phase separations and multiple azeotropic distillation trains.

16 Claims, 1 Drawing Sheet

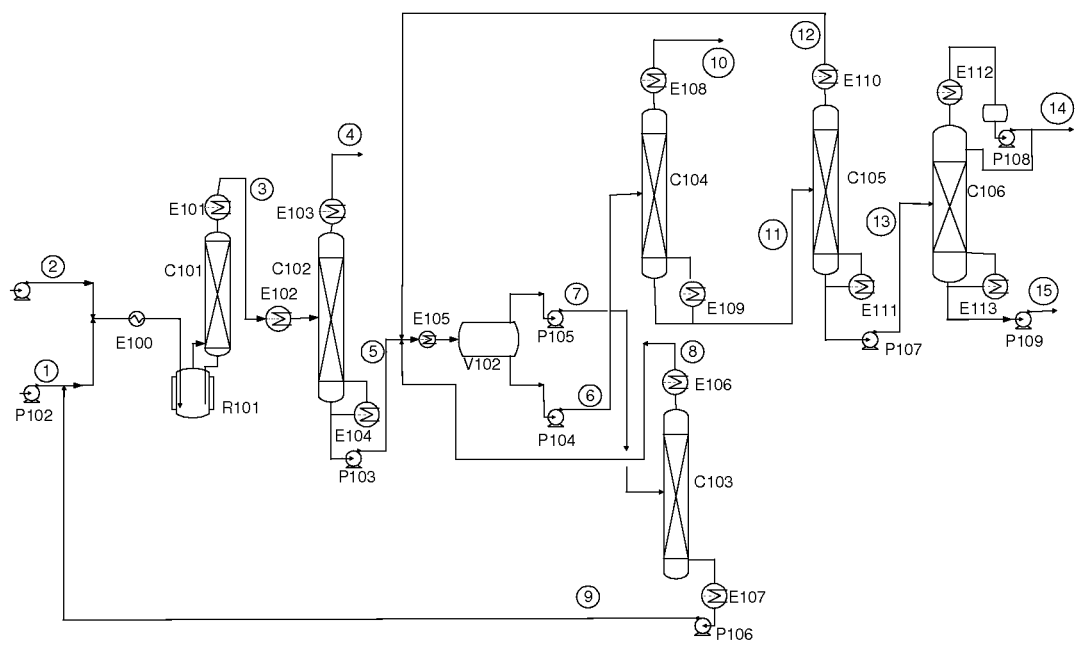

SEPARATION OF R-1233 FROM HYDROGEN FLUORIDE

This application is a Continuation-In-Part of U.S. application Ser. No. 13/257,740 filed Sep. 20, 2011, which claims priority to International application serial number PCT/US10/27409 filed Mar. 16, 2010 which designated the United States which claims priority of U.S. provisional application Ser. No. 61/162,789 filed Mar. 24, 2009, all incorporated herein by reference.

FIELD OF THE INVENTION

The present invention relates to a separation method for isolating monochloro-trifluoropropenes such as 1,1,1-trifluoro-3-chloro-2-propene (HCFC-1233zd) from azeotropic or near azeotropic streams of monoehloro-trifluoropropenes and hydrogen fluoride. The method of the present invention makes use of chilled, liquid phase separation combined with azeotropic distillations to isolate pure monochloro-trifluoropropenes such as HCFC-1233zd.

BACKGROUND OF THE INVENTION

With continued regulatory pressure there is a growing need to produce more environmentally sustainable replacements for refrigerants, heat transfer fluids, foam blowing agents, solvents, and aerosols with lower ozone depleting and global warming potentials. Chlorofluorocarbon (CFC) and hydrochlorofluorocarbons (HCFC), widely used for these applications, are ozone depleting substances and are being phased out in accordance with guidelines of the Montreal Protocol. Hydrofluorocarbons (HFC) are a leading replacement for CFCs and HCFCs in many applications; though they are deemed "friendly" to the ozone layer they still generally possess high global warming potentials. One new class of compounds that has been identified to replace ozone depleting or high global warming substances are halogenated olefins, such as hydrofluoroolefins (HFO) and hydrochlorofluoroolefins (HCFO). The HFOs and HCFOs provide the low global warming potential and zero or near zero ozone depletion properties desired.

Because of the presence of alkene linkage it is expected that the HFOs and HCFOs will be chemically unstable, relative to HCFCs or CFCs. The inherent chemical instability of these materials in the lower atmosphere results in short atmospheric lifetimes, which provide the low global warming potential and zero or near zero ozone depletion properties desired.

U.S. Pat. No. 6,013,846 discloses azeotropes of HF and 1233zd and methods for separating such azeotropes from mixtures of HF and 1233zd which are HF rich or 1233zd rich. The method comprises treating a mixture rich in HF relative to the azeotrope of 1233zd and HF in a distillation (rectification) column to obtain a distillate containing the azeotrope and a bottoms product of relatively pure HF

SUMMARY OF THE INVENTION

In the present invention, a method was discovered for separating azeotrope or near azeotrope compositions of monochloro-trifluoropropenes and HF, preferrably 1.233zd and HF. The method of the present invention is also effective in separating other isomers of 1233, such as 1233xf (1,1,1-trifluoro-2-chloro-3-propene) from azeotrope or azeotrope like combinations with HF. The azotrope or near azeotrope combination of monochloro-trifluoropropenes and HP could be produced, for example, in a liquid phase fluorination reaction of 1,1,1,3,3-pentachloropropane (240fa) or 1,1,3,3-tetrachloro-2-propene (referred to hereinafter as (1230za). The 1230za is of special interest as a starting material since it has been shown to fluorinate readily in the liquid phase without a catalyst, as taught in U.S. Pat. No. 5,877,359. One of the problems associated with the production of the trans isomer of 1233zd, the preferred isomer of the present invention, is that it has nearly the same boiling point (18-20° C.) as HP and azeotropes or near azeotropes can form with HF.

The fluorination of 240fa 1230za can take place in a catalyzed or uncatalyzed liquid phase reaction. Typically the liquid phase fluorination reactor is coupled to a rectification column(s). The feed to the fluorination reactor consists of an organic chlorocarbon and HP which react to form a hydrofluorocarbon (HIV) or hydrochlorofluorocarbon (HUG) that is more volatile than the original chlorocarbon. The HFC or HCFC product can be removed from the reaction mixture as a gas along with by-product HCl and some unreacted HF. The rectification column is coupled to the reactor to separate unreacted organic and under fluorinated organic compounds from HCl. The overhead from the rectification column is an azeotrope or near azeotrope combination of 1233zd and which also contains the HCl by-product of the reaction. In the case of 1233zd, the organic feedstock chlorocarbon to the fluorination reactor can be 1,1,3,3 tetrachloropropene (1230za) or 1,1,1,3,3 pentachloropropane (240fa).

In the present application "distillation column" and "rectification column" are sometimes used interchangeably. Actually, however, a rectification column is a specific type of distillation column. In most distillation columns the material to be distilled is fed to the middle of the column; below the feed point is called the stripping section and above the feed point is called the rectification section. Reference is made herein to a rectification column when the material to be distilled is fed to the bottom of the "distillation column."

The process of the present invention uses azeotropic distillation columns to separate 1233zd from HF. The composition of the feed to the azeotropic columns must have either HF or F1233zd in substantial excess of its azeotropic composition. In the method of the present invention, such streams are provided by first separating, by distillation, HCl from the azeotrope or near azeotrope 1233zd/HF that exits from the overhead of the rectification column. The azeotrope or near azeotrope combination of 1233zd/HF is than cooled to a temperature sufficient to provide separation into an HF rich phase and a 1233zd rich phase. The HF rich phase is separated from the 1233zd rich phase in a liquid phase separator. Thereafter, the HF rich phase is fed to a first azeotropic distillation column that removes the azeotrope as an overhead and pure HF as the bottoms. The 1233zd rich phase is sent to a distillation train that includes a second azeotropic distillation column. The distillation train separates the 1233zd/HF azeotrope from 1233zd via azeotropic distillation and also separates impurities from the 1233zd to provide a stream of substantially pure 1233zd.

BRIEF DESCRIPTION OF THE DRAWINGS

FIG. 1 is a schematic of a typical process in accordance with the present invention.

DETAILED DESCRIPTION OF THE INVENTION

The object of the present invention is to provide a means for separating monochloro-trifluoropropenes, preferably 1,1,1-trifluoro-3-chloro-2-propene (1233zd) and more preferably the trans isomer of 1233zd referred to hereinafter as "1233zd-t", from HF when the two occur in an azeotrope or near azeotropic combinations. Azeotropic distillation is used to separate RIF and 1233zd, preferably 1233zd-t, since they have very similar boiling points. The azeotropic mixture is typical of what is produced from liquid phase reactions that produce 1233zd from organic chlorocarbon feedstocks such as 1230za and 240fa. The azeotrope or near azeotrope compositions form when the reactor system uses a rectification column coupled to the reactor to separate out unreacted unreacted feed organic, and under fluorinated organics from the vapor produced. The rectification column separates the vapor effluent from the reactor and produces a gas phase combination of HF and 1233zd, preferably 1233zd-t, in a ratio near the azeotropic ratio of HF and 1233zd. U.S. Pat. No. 6,013,846 discloses that this is ratio is about 2.33 moles HF per mole of 1233zd at 50° C. The overhead from such rectification columns would also contain HCl.

In accordance with the present invention, the azeotropic or near azeotropic combination of 1233zd, preferably 1233zd-t, and HF from the top of the rectification column is fed to a distillation column where HCl is removed. The HCl removal distillation column is typically operated at pressures of from about 100 psig to 300 psig. The bottoms from the HCl removal distillation column comprises the azeotrope or azeotrope like combination of 1233zd, preferably 1233zd-t, and HF. This bottoms stream is cooled sufficiently to provide that two phases form. Each phase contain the azeotrope or azeotrope like 1233zd/HF and independently HE or 1233zd. Thus the overall composition of each stream differs significantly from the azeotrope. One phase, the lighter phase, is rich in HF and the second phase, the heavier phase, is rich 1233zd, preferably 1233zd-t. The two phase mixture is fed to a liquid phase separator. The liquid phase separator can be operated at temperatures of from about −60° C. to +50° C., preferably from about −20° to +10° C. The lighter liquid phase has HF in substantial excess over the azeotrope composition. This HF rich phase is sent to a first azeotropic distillation column where azeotropic 1233zd/HF is removed as overhead and relatively pure HF removed as the bottoms. The azeotropic 1233zd/HF overhead is recycled to cooled and fed to the phase separator and the HE bottoms stream is recycled to the reactor. The heavy phase from the liquid phase separator comprises a substantial excess of 1233zd-t, preferably 1233zd-t, over the azeotropic composition. This stream is sent to a distillation train comprising a series of distillation columns. The first distillation column removes as an overhead any very volatile impurities such as HCl or over fluorinated HFC's. The bottoms of this column is sent to a second azeotropic column. This second azeotropic distillation column removes a 1233zd/HF azeotrope as overhead and crude 1233zd, preferably 1233zd-t, as a bottoms. The overhead can be recycled to be cooled and fed to the liquid phase separator. The bottoms is sent to a product recovery distillation column that recovers purified 1233zd, preferably 1233zd-t, as overhead and any heavy, organic impurities such as the cis-isomer of 1233zd as a bottoms stream. The process of the present invention provides a method whereby relatively pure 1233zd, preferably 1233zd-t, can be separated from an azeotrope azeotrope like combination of 1233zd and HF.

FIG. 1 show a schematic of a process in accordance with the present invention. The feeds to the reactor system are typically HF (Stream 1) and an organic stream, either 240fa or 1230za (Stream 2). The reactor (R101) may or may not contain a catalyst. The selective products of the reaction are 1233zd and HCl. These would exit the reaction system from the top of a rectification Column (C101) along with enough HF to be close to its azeotropic ratio with 1233zd (Stream 3).

Column C102 removes the HCl as an overhead product (Stream 4). This could be done at pressures anywhere from 100 psig to 300 psig. The bottoms from this column (stream 5) would then be cooled in a heat exchanger (E105) and sent to a liquid phase separator (V102). The liquid phase separator could operate at temperatures from −60° C. to +50° C. A preferred temperature range would be −20° C. to 10° C. The lighter liquid phase (Stream 7) would have HF in substantial excess over the azeotropic composition. This phase is sent to a first azeotropic distillation column (C103) that removes the HF/F1233zd azeotrope as overhead (Stream 8) and relatively pure HF as a bottoms (Stream 9). The azeotropic composition is recycled to be cooled and fed to the phase separator and the HF can be recycled to the reactor R101.

The heavy phase (Stream 6) from the phase separator contains 1233zd in substantial excess over the 1233zd/HF azeotropic composition. This stream is sent to a series of distillation columns. The first column (C104) is a purification column which removes as an overhead (Stream 10) any very volatile impurities such as residual HCl or over fluorinated HFC's. The bottoms of the first column (Stream 11) is then sent to the second azeotropic distillation column (C105). This azeotropic distillation column removes a 1233zd/HF azeotrope as overhead (Stream 12) and a crude 1233zd stream as bottoms (Stream 13). The overhead stream can be recycled to be cooled and fed to the liquid phase separator V102. The bottoms stream is sent to a product recovery distillation column (C106) that recovers pure 1233zd, preferably 1233zd-t, as overhead (Stream 14) and any organic impurities such as the cis isomer of 1233zd as a bottoms (Stream 15).

As shown in Example 1, the heavy phase (stream 6) effluent from the phase separator can have a relatively low concentration of HF. Recovery of such small amounts of HF may not be desirable. Consequently, an alternative to distillation of that stream to remove and recover the HF is to remove the HF using absorption into liquid absorbent such as water or caustic, NaOH and/or KOH, or adsorption onto a solid adsorbent such as alumina and discard the adsorbed HF. The HF (acid) free stream remaining would flow to the first column (C104). The lighter phase (stream 7) contains a significant amount of F1233zd-t. An alternative to treatment in a dedicated azeotropic distillation column (C103) for the heaver phase is to recycle this stream to the bottom portion of column C101 (i.e. the rectification column) where the HF is separated and sent back to the reactor and the F1233zd/HF azeotrope is distilled overhead.

EXAMPLES

Example 1

A set of experiments were conducted to determine the liquid-liquid equilibrium in an HF-F1233zd system. A mixture of F1233zd and HF were equilibrated at four different temperatures. Samples of bottom and top phases were analyzed. The following results were obtained:

TABLE 1

| T (Deg C.) | Upper Layer (wt %) | | Lower Layer (wt %) | |
| --- | --- | --- | --- | --- |
| | HF | F1233zd-t | HF | F1233zd-t |
| −30 | 75.72 | 24.28 | 0.85 | 99.15 |
| −15 | 71.16 | 28.84 | 1.18 | 98.82 |

TABLE 1-continued

|  | Upper Layer (wt %) | | Lower Layer (wt %) | |
| --- | --- | --- | --- | --- |
| T (Deg C.) | HF | F1233zd-t | HF | F1233zd-t |
| 0 | 67.86 | 32.14 | 1.72 | 98.28 |
| 30 | 56.26 | 43.74 | 4.12 | 95.88 |

Example 2

An example of a material balance of the relevant part of the process for a phase separator operated at −20 C is shown in Table 1 The stream numbers refer to those used in FIG. 1. As the table shows, the phase separation will produce two phases far enough removed from the azeotropic composition that aeotropic distillation can be used to isolate both pure HF and pure 1233zd.

TABLE 2

|  | kg/hr | | | | | | | | |
| --- | --- | --- | --- | --- | --- | --- | --- | --- | --- |
|  | 5 Feed | 6 Org Ph | 7 HF Ph | 8 HF Ovhd | 9 HF Bttms | 10 Lights Ovhd | 11 Lights Btms | 12 F12333zd Ovhd | 13 F1233zd Bttms |
| 1233zd-t | 130.45 | 134.93 | 25.32 | 25.32 | 0.00 | 0.00 | 134.93 | 4.48 | 130.45 |
| 1233zd-c | 13.05 | 13.40 | 2.52 | 2.52 | 0.00 | 0.00 | 13.40 | 0.36 | 13.05 |
| 245fa | 0.00 | 0.00 | 0.00 | 0.00 | 0.00 | 0.00 | 0.00 | 0.00 | 0.00 |
| HF | 57.20 | 1.79 | 68.29 | 11.10 | 57.20 | 0.00 | 1.79 | 1.79 | 0.00 |
| HCl | 0.36 | 0.36 | 0.00 | 0.00 | 0.00 | 0.36 | 0.00 | 0.00 | 0.00 |
| Total | 201.06 | 150.48 | 96.13 | 38.93 | 57.20 | 0.36 | 150.11 | 6.62 | 143.50 |
| Temp (C.) | −20 | −20 | −20 | 47 | 68 | −28 | 80 | 65 | 65 |
| Press (psia) | 40 | 40 | 40 | 65 | 66 | 130 | 130 | 50 | 88 |

While the present invention has been described with respect to particular embodiments thereof, it is apparent that numerous other forms and modifications of this invention will be obvious to those skilled in the art. The appended claims and this invention generally should be construed to cover all such obvious forms and modifications, which are within the true spirit and scope of the present invention.

The invention claimed is:

1. A method for producing monochloro-trifluoropropene from an azeotrope or azeotrope like combination of monochloro-trifluoropropene and HF which comprises (a) distilling a reaction mixture comprising hydrogen fluoride, monochloro-trifluoropropene, and hydrogen chloride to remove hydrogen chloride as overhead and a bottoms stream, (b) cooling the bottoms stream to form two liquid phases, (c) separating said two liquid phases in a liquid phase separator into a first light phase comprising hydrogen fluoride in excess over an azeotrope or azeotrope like combination of monochloro-trifluoropropene and hydrogen fluoride and a second heavy phase comprising an excess of monochloro-trifluoropropene over an azeotrope or azeotrope like combination of monochloro-trifluoropropene, (d) distilling said first light phase in a distillation column to produce a top stream of an azeotrope of monochloro-trifluoropropene and hydrogen fluoride and a bottoms stream of hydrogen fluoride, (e) contacting said second heavy phase with an absorbent to remove HF followed by distilling said second heavy phase in a distillation train to provide a monochloro-trifluoropropene stream.

2. The method of claim 1 wherein said reaction mixture comprising hydrogen fluoride, monochloro-trifluoropropene, and hydrogen chloride is formed by reacting 1,1,1,3,3-pentachloropropane and/or 1,1,3,3-tetrachloro-2-propene and hydrogen fluoride in a reactor.

3. The method of claim 1 wherein said bottoms stream is cooled to from about −60 to +30 degrees C.

4. The method of claim 1 wherein said top stream of an azeotrope of monochloro-trifluoropropene and hydrogen fluoride is recycled to said liquid phase separator.

5. The method of claim 2 wherein said bottoms stream of hydrogen fluoride is recycled to said reactor.

6. The method of claim 1 wherein said distillation train comprises a purification distillation column to separate said excess of monochloro-trifluoropropene over an azeotrope or azeotrope like combination of monochloro-trifluoropropene and hydrogen fluoride into a volatile impurities top stream and a bottoms stream which is sent to a second azeotropic distillation column to provide a top stream of an azeotrope of monochloro-trifluoropropene and hydrogen fluoride and a bottoms stream of crude monochloro-trifluoropropene and a recovery distillation column to separate said bottoms stream of crude monochloro-trifluoropropene into a top stream of purified monochloro-trifluoropropene and a bottoms stream of heavy impurities.

7. The method of claim 1 wherein said monochloro-trifluoropropene is selected from the group 1,1,1-trifluoro-3-chloro-2-propene and 1,1,1-trifluoro-2-chloro-3-propene.

8. The method of claim 6 wherein said purified monochloro-trifluoropropene is the trans isomer of 1,1,1-trifluoro-3-chloro-2-propene.

9. The method of claim 1 wherein said absorbent is a liquid absorbent selected from the group consisting of water, aqueous NaOH, aqueous KOH and mixtures thereof.

10. The method of claim 1 wherein said absorbent is an alumina solid absorbent.

11. A method for producing monochloro-trifluoropropene from an azeotrope or azeotrope like combination of monochloro-trifluoropropene and HF which comprises (a) distilling a reaction mixture comprising hydrogen fluoride, monochloro-trifluoropropene, and hydrogen chloride in a rectification column to remove hydrogen chloride as overhead and a bottoms stream, (b) cooling the bottoms stream to form two liquid phases, (c) separating said two liquid phases in a liquid phase separator into a first light phase comprising hydrogen fluoride in excess over an azeotrope or azeotrope like combination of monochloro-trifluoropropene and hydrogen fluoride and a second heavy phase comprising an excess of monochloro-trifluoropropene over an azeotrope or azeotrope like combination of monochloro-trifluoropropene, (d) recycling said first light phase to said rectification column, (e)

distilling said second heavy phase in a distillation train to provide a monochloro-trifluoropropene stream.

12. The method of claim 11 wherein said reaction mixture comprising hydrogen fluoride, monochloro-trifluoropropene, and hydrogen chloride is formed by reacting 1,1,1,3,3-pentachloropropane and/or 1,1,3,3-tetrachloro-2-propene and hydrogen fluoride in a reactor.

13. The method of claim 11 wherein said bottoms stream is cooled to from about −60 to +30 degrees C.

14. The method of claim 11 wherein said distillation train comprises a purification distillation column to separate said excess of monochloro-trifluoropropene over an azeotrope or azeotrope like combination of monochloro-trifluoropropene and hydrogen fluoride into a volatile impurities top stream and a bottoms stream which is sent to a second azeotropic distillation column to provide a top stream of an azeotrope of monochloro-trifluoropropene and hydrogen fluoride and a bottoms stream of crude monochloro-trifluoropropene and a recovery distillation column to separate said bottoms stream of crude monochloro-trifluoropropene into a top stream of purified monochloro-trifluoropropene and a bottoms stream of heavy impurities.

15. The method of claim 11 wherein said monochloro-trifluoropropene is selected from the group 1,1,1-trifluoro-3-chloro-2-propene and 1,1,1-trifluoro-2-chloro-3-propene.

16. The method of claim 15 wherein said monochloro-trifluoropropene is the trans isomer of 1,1,1-trifluoro-3-chloro-2-propene.

* * * * *